United States Patent
Shinada (10) Patent No.: US 10,436,751 B2
(45) Date of Patent: Oct. 8, 2019

(54) DIELECTRIC BARRIER DISCHARGE IONIZATION DETECTOR

(71) Applicant: Shimadzu Corporation, Kyoto (JP)

(72) Inventor: Kei Shinada, Kyoto (JP)

(73) Assignee: Shimadzu Corporation, Kyoto (JP)

(*) Notice: Subject to any disclaimer, the term of this patent is extended or adjusted under 35 U.S.C. 154(b) by 4 days.

(21) Appl. No.: 15/698,368

(22) Filed: Sep. 7, 2017

(65) Prior Publication Data
US 2018/0067080 A1    Mar. 8, 2018

(30) Foreign Application Priority Data

Sep. 8, 2016 (JP) ................. 2016-175503

(51) Int. Cl.
  *G01N 27/68* (2006.01)
  *G01N 27/60* (2006.01)
  (Continued)

(52) U.S. Cl.
  CPC .......... *G01N 27/68* (2013.01); *G01N 27/60* (2013.01); *G01N 27/70* (2013.01); *G01N 30/64* (2013.01);
  (Continued)

(58) Field of Classification Search
  CPC .... G01N 27/68; G01N 33/0027; G01N 27/60; G01N 27/70; G01N 30/64; G01N 2030/025; G01R 19/0061
  See application file for complete search history.

(56) References Cited

U.S. PATENT DOCUMENTS

| 4,282,521 A | 8/1981 | Lieberman |
| 6,489,585 B1 | 12/2002 | Nakamura et al. |
| (Continued) | | |

FOREIGN PATENT DOCUMENTS

| CN | 102368060 A | 3/2012 |
| CN | 102866224 A | 1/2013 |
| (Continued) | | |

OTHER PUBLICATIONS

Kogelschatz, Dielectric-barrier Discharges: Their History, Discharge Physics, and Industrial Applications, Plasma Chemistry and Plasma Processing, vol. 23, No. 1, Mar. 2003 (Year: 2003).*
(Continued)

*Primary Examiner* — Daniel R Miller
(74) *Attorney, Agent, or Firm* — Maier & Maier, PLLC (57) ABSTRACT

A dielectric barrier discharge ionization detector Includes: a dielectric tube; a high-voltage electrode connected to an AC power source and circumferentially formed on the outer wall of the dielectric tube; upstream-side and downstream-side ground electrodes and circumferentially formed above and below the high-voltage electrode; a discharging section for generating electric discharge to create plasma, from a gas containing argon; and a charge-collecting section for ionizing sample-gas components by the plasma and detecting an ion current formed by the ionized components. The detector also satisfies one or both of the following conditions: the upstream-side ground electrode is longer than a creeping discharge initiation distance between a tube-line tip member at the upper end of the dielectric tube and the high-voltage electrode; or the downstream-side ground electrode is longer than a creeping discharge initiation distance between the high-voltage electrode and the charge-collecting section.

2 Claims, 8 Drawing Sheets

(51) Int. Cl.
*G01N 27/70* (2006.01)
*G01N 30/64* (2006.01)
*G01N 33/00* (2006.01)
G01N 30/02 (2006.01)
G01R 19/00 (2006.01)

(52) U.S. Cl.
CPC ... *G01N 33/0027* (2013.01); *G01N 2030/025* (2013.01); *G01N 2030/647* (2013.01); *G01R 19/0061* (2013.01)

(56) References Cited

U.S. PATENT DOCUMENTS

| | | | |
|---|---|---|---|
| 2009/0236042 A1* | 9/2009 | Wada | C01B 13/11 156/345.43 |
| 2010/0320916 A1 | 12/2010 | Yagi et al. | |
| 2011/0168881 A1 | 7/2011 | Sturgeon et al. | |
| 2011/0260732 A1* | 10/2011 | Shinada | G01N 27/70 324/464 |
| 2011/0316552 A1 | 12/2011 | Shinada et al. | |
| 2013/0154658 A1 | 6/2013 | Shinada et al. | |
| 2014/0145724 A1 | 5/2014 | Shinada et al. | |
| 2015/0369777 A1 | 12/2015 | Shinada et al. | |
| 2017/0292904 A1 | 10/2017 | Xing et al. | |
| 2018/0067079 A1 | 3/2018 | Shinada et al. | |
| 2018/0067081 A1 | 3/2018 | Shinada et al. | |
| 2018/0067082 A1 | 3/2018 | Shinada et al. | |
| 2018/0067083 A1 | 3/2018 | Shinada et al. | |

FOREIGN PATENT DOCUMENTS

| | | |
|---|---|---|
| JP | 2010-060354 A | 3/2010 |
| JP | 2013-125022 A | 6/2013 |
| WO | 2012/169419 A1 | 12/2012 |

OTHER PUBLICATIONS

Office Action dated Nov. 1, 2018 in corresponding U.S. Appl. No. 15/698,312; 12 pages.
Office Action dated Nov. 1, 2018 in corresponding U.S. Appl. No. 15/698,351; 12 pages.
Kogelschatz, Ulrich, "Dielectric-barrier Discharges: Their History, Discharge Physics, and Industrial Applications", Plasma Chemistry and Plasma Processing, vol. 23, No. 1, Mar. 2003, 49 pages.
Notice of Allowance dated Oct. 17, 2018 in corresponding U.S. Appl. No. 15/698,391; 13 pages.
Shinada et al., "Development of New Ionization Detector for Gas Chromatography by Applying Dielectric Barrier Discharge", Shimadzu Flyouron (Shimadzu Review), vol. 69, Nos. 3/4, Mar. 29, 2013, pp. 255-263.
Office Action dated May 28, 2019, in corresponding Chinese Application No. 201710798481.9 including partial machine-generated English-language translation; 9 pages.
Office Action dated Jun. 11, 2019, in corresponding U.S. Appl. No. 15/698,351; 12 pages.
Notice of Allowance dated Jun. 14, 2019 in corresponding U.S. Appl. No. 15/698,312; 19 pages.
Office Action dated Jun. 14, 2019 in corresponding U.S. Appl. No. 15/698,331; 20 pages.

* cited by examiner

DIELECTRIC BARRIER DISCHARGE IONIZATION DETECTOR

TECHNICAL FIELD

The present invention relates to a dielectric barrier discharge ionization detector which is primarily suitable as a detector for a gas chromatograph (GC).

BACKGROUND ART

In recent years, dielectric barrier discharge ionization detectors (which are hereinafter abbreviated as the "BIDs") employing the ionization by dielectric barrier discharge plasma have been put to practical use as a new type of detector for GC (for example, see Patent Literatures 1 and 2 as well as Non Patent Literature 1).

BIDs described in the aforementioned documents are roughly composed of a discharging section and a charge-collecting section which is located below the discharging section. In the discharging section, a low-frequency AC high voltage is applied to plasma-generating electrodes circumferentially formed around a tube made of a dielectric material, such as quartz glass ("dielectric tube"), to ionize an inert gas supplied into the tube line of the dielectric tube and thereby form atmospheric-pressure non-equilibrium plasma. Due to the effects of the light emitted from this plasma (vacuum ultraviolet light), excited species and other elements, the sample components in a sample gas introduced into the charge-collecting section are ionized. The resulting ions are collected through a collecting electrode to generate detection signals corresponding to the amount of ions, i.e. the amount of sample components.

Figure 8:
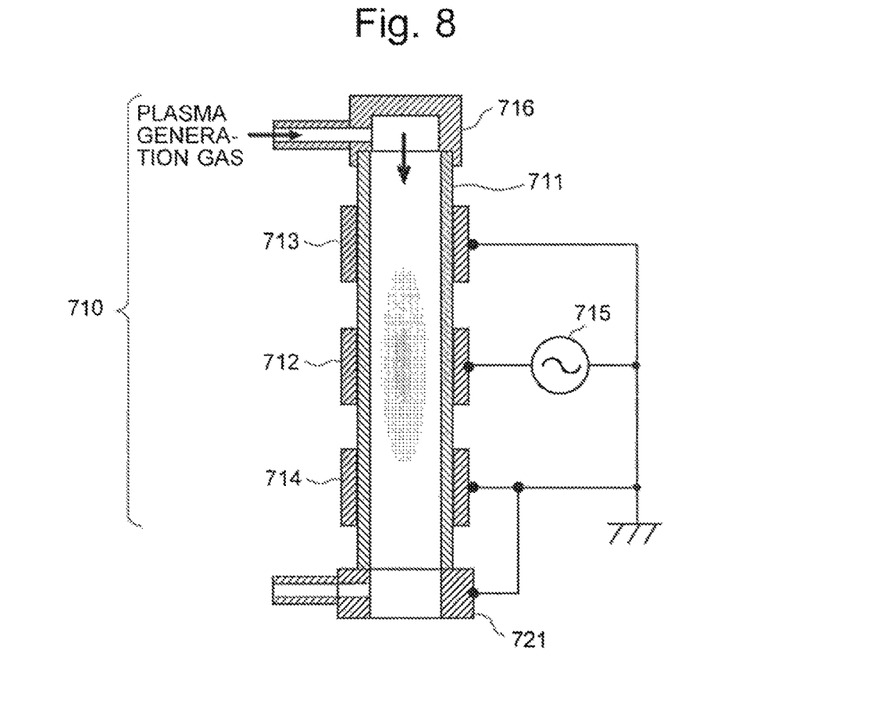
FIG. 8 is a schematic configuration diagram of the discharging section and surrounding area in a conventional BID.

FIG. 8 shows the configuration of the discharging section and surrounding area in the aforementioned BID. As noted earlier, the discharging section 710 includes a cylindrical dielectric tube 711 made of a dielectric material, such as quartz, the inner space of which forms a passage of inert gas serving as plasma generation gas. On the outer wall surface of the cylindrical dielectric tube 711, three ring-shaped metallic electrodes (made of stainless steel, copper or the like) are circumferentially formed at predetermined intervals of space. A high AC excitation voltage power source 715 for generating a low-frequency high AC voltage is connected to the central electrode 712 among the three electrodes, while the electrodes 713 and 714 located above and below the central electrode are both grounded. Hereinafter, the central electrode is called the "high-voltage electrode" 712, while the upper and lower electrodes are called the "ground electrodes" 713 and 714. The three electrodes are collectively referred to as the plasma generation electrodes. Since the wall surface of the cylindrical dielectric tube 711 is present between the passage of the inert gas and the plasma generation electrodes, the dielectric wall itself functions as a dielectric coating layer which covers the surface of those electrodes 712, 713 and 714, enabling a dielectric barrier discharge to occur. With the inert gas flowing through the cylindrical dielectric tube 711, when the high AC excitation voltage power source 715 is energized, a low-frequency high AC voltage is applied between the high-voltage electrode 712 and each of the upper and lower ground electrodes 713 and 714 located above and below. Consequently, an electric discharge occurs within the area sandwiched between the two ground electrodes 713 and 714. This electric discharge is induced through the dielectric coating layer (the wall surface of the cylindrical dielectric tube 711), and therefore, is a form of dielectric barrier discharge, whereby the plasma generation gas flowing through the cylindrical dielectric tube 711 is ionized over a wide area, forming a cloud of plasma (atmospheric-pressure non-equilibrium plasma).

The two ground electrodes 713 and 714 arranged so as to sandwich the high-voltage electrode 712 in between prevents the plasma generated by the electric discharge from spreading into the upstream and downstream sections of the cylindrical dielectric tube 711, whereby the effective plasma generation area is confined to the space between the two ground electrodes 713 and 714.

In the BID, the dielectric material which covers the surface of the plasma generation electrodes in the previously described manner prevents an emission of thermions or secondary electrons from the surface of the metallic electrodes. Furthermore, since the plasma generated by the dielectric barrier discharge is a non-equilibrium plasma with low-temperature neutral gas, various factors which cause a fluctuation of the plasma, are suppressed, such as a temperature fluctuation in the discharging section 710 or an emission of gas from the inner wall of the quartz tube due to the heat. As a result, the BID can maintain plasma in a stable form and thereby achieve a higher level of signal-to-noise (SN) ratio than the flame ionization detector (FID), which is the most commonly used type of detector for GC.

In general, there are two types of "dielectric barrier discharge"; an electric discharge generated by a configuration in which only one of the high-voltage and ground electrodes is covered with a dielectric body (which is hereinafter called the "single-side barrier discharge"); and an electric discharge generated by a configuration in which both of the high-voltage and ground electrodes are covered with a dielectric body (which is hereinafter called the "double-side barrier discharge". Non Patent Literature 1 discloses the result of a study in which two discharging sections respectively employing those two configurations were constructed and their detector outputs in a BID-equivalent structure were compared, which demonstrated that a higher SN ratio could be achieved with the double-side barrier discharge than with the single-side barrier discharge.

As the inert gas for plasma generation in such a BID, helium (He) gas or argon (Ar) gas (or He gas with a trace amount of Ar gas added) is particularly widely used in practice. The reasons for using those gases are as follows:

(1) He gas: The discharge light generated by using He gas has an extremely high energy level of approximately 17.7 eV, making it possible to ionize and detect the atoms and molecules of most substances except for neon (Ne) and He. This is particularly useful for the detection of inorganic substances, since FIDs cannot ionize (and therefore cannot detect) inorganic substances.

(2) Ar gas (or He gas with a trace amount of Ar gas added): The energy level of discharge light generated by using Ar gas is approximately 11.7 eV and cannot ionize inorganic substances, as with the FID. This characteristic is useful in the case of specifically detecting organic substances. For example, in the case of detecting a trace amount of organic substance in an aqueous solution, the trace amount of organic substance of interest can be easily detected since the water used as the solvent cannot be detected.

Since the discharge characteristics vary depending on the kind of gas, the optimum electrode arrangement (e.g. the width of each electrode and the spacing of the electrodes) in the discharging section of the BID also changes depending on whether He gas or Ar gas is used as the inert gas. Accordingly, BIDs are configured to allow users to prepare a plurality of cylindrical dielectric tubes with different electrode arrangements and select a cylindrical dielectric tube having a suitable electrode arrangement for the kind of gas to be used. In the following description, a BID which uses Ar gas (or He gas with a trace amount of Ar gas added) as the plasma generation gas is called the "Ar-BID". Similarly, a BID which uses He gas as the plasma generation gas is called the "He-BID".

Figure 9:
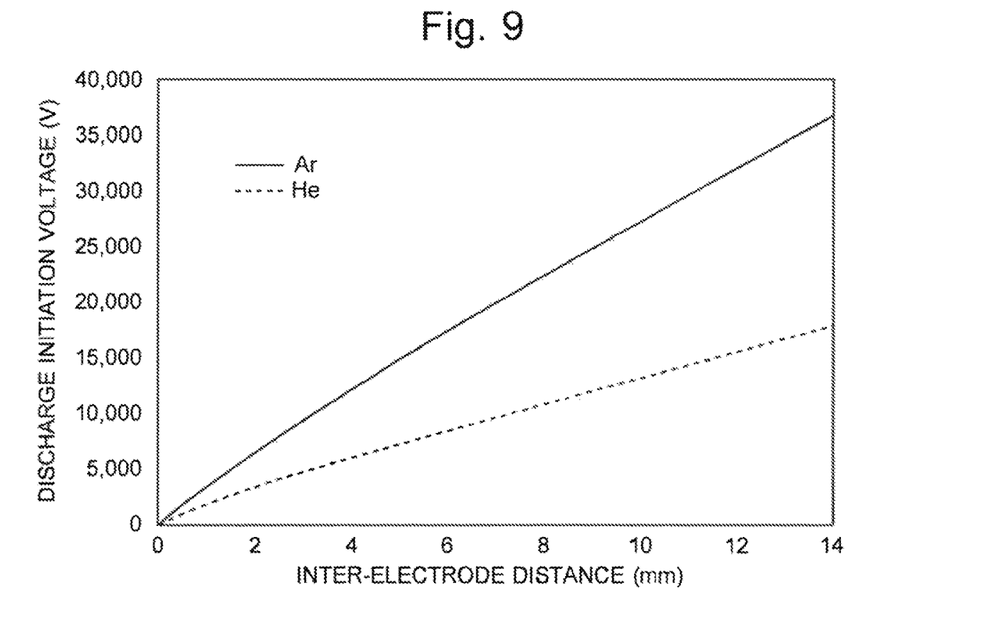
FIG. 9 is a graph showing the relationship between the discharge initiation voltage for spark discharge in Ar and He at atmospheric pressure and the inter-electrode distance.

FIG. 9 is a graph obtained by plotting the discharge initiation voltage for He and Ar at atmospheric pressure against the inter-electrode distance based on Paschen's law which is an empirical law concerning the discharge voltage for spark discharge. As can be seen in the graph, when the inter-electrode distance is the same, the discharge initiation voltage for Ar is approximately two times as high as the discharge initiation voltage for He. In other words, provided that the device should be operated at the same discharge initiation voltage, the inter-electrode distance for Ar needs to be equal to or shorter than one half of the distance for He. Since there are also other parameters affecting the dielectric barrier discharge employed in BIDs, such as the material of the dielectric body, gas purity, frequency of the discharge power source, and waveform of the power source, it is difficult to predict an optimum electrode arrangement and discharging conditions from Paschen's law which is the empirical law concerning spark discharge. However, from the foregoing discussion, it is at least possible to conclude that if the discharge voltage is the same, the Ar-BID requires a shorter inter-electrode distance between the plasma generation electrodes than the He-BID (otherwise the discharge voltage needs to be increased).

CITATION LIST

Patent Literature

Patent Literature 1: JP 2010-60354 A
Patent Literature 2: WO 2012/169419 A
Patent Literature 3: JP 2013-125022 A Non Patent Literature Non Patent Literature 1: Shinada and four other authors, "Development of New Ionization Detector for Gas Chromatography by Applying Dielectric Barrier Discharge", *Shimadzu Hyouron* (*Shimadzu Review*), Vol. 69, Nos. 3/4, Mar. 29, 2013

SUMMARY OF INVENTION

Technical Problem

Due to the previously described reason, the distance between the neighboring electrodes in conventional Ar-BIDs has been made shorter than in He-BIDs. However, an Ar-BID configured in this manner has an evidently lower SN ratio than He-BIDs.

The present invention has been developed in view of the previously described point. Its objective is to provide an Ar-BID capable of achieving a high level of SN ratio.

Solution to Problem

A study to search for the cause of such a decrease in the SN ratio in the Ar-BID has experimentally revealed the fact that, in the case of the electric discharge in Ar gas, although the inter-electrode distance at which the electric discharge can occur is short as noted earlier, once the electric discharge is initiated, the plasma generation area spreads over the entire cylindrical dielectric tube 711 and eventually reaches the tube-line tip member 716 provided at the upper end of the cylindrical dielectric tube 711 as well as the connection member 721 of the charge-collecting section connected to the lower end of the cylindrical dielectric tube 711. Since the tube-line tip member 716 and the connection member 721 are both made of metal and electrically grounded, the electric discharge which occurs within the cylindrical dielectric tube 711 in the aforementioned situation becomes a single-side barrier discharge between the high-voltage electrode 712 which is covered with the dielectric body and the tube-line tip member 716 or connection member 721 which is not covered with any dielectric body. This is the likely reason why the SN ratio was lower than in the case of the double-side barrier discharge.

The present inventor has inferred that the aforementioned expansion of the plasma generation area beyond the range estimated by Paschen's law occurs due to the creeping discharge occurring at the interface between the inner wall of the cylindrical dielectric tube 711 and the Ar gas. Creeping discharge is a discharge phenomenon which occurs along the boundary surface between different dielectrics. In Ar-BIDs, it is likely that this phenomenon develops from the high-voltage electrode 712 into the upper and lower directions, to eventually induce a gas discharge between the high-voltage electrode 712 and the tube-line tip member 716 as well as between the high-voltage electrode 712 and the charge-collecting section. That is to say, in the aforementioned Ar-BID, since the tube-line tip member 716 and the metallic member (connection member 721) connected to the lower end of the cylindrical dielectric tube 711 are electrically grounded, a potential gradient is formed from the high-voltage electrode 712 toward each of those members 716 and 721. If the ground electrodes 713 and 714 provided between the high-voltage electrode 712 and each of those members 716 and 721 are sufficiently long, the reference potential is spread over a wide range within the space between the high-voltage electrode 712 and each of those members 716 and 721, preventing the development of the creeping discharge. However, in the previously described conventional Ar-BID, since the ground electrodes 713 and 714 are not sufficiently long, the creeping discharge originating from the high-voltage electrode 712 can develop beyond the areas where the ground electrodes 713 and 714 are located, to eventually reach the tube-line tip member 716 or the charge-collecting section, causing the aforementioned expansion of the plasma generation area. Based on such an inference, the present inventor has compared the initiation distance for the creeping discharge in the Ar gas and the same distance in the He gas. The result confirmed that the creeping discharge initiation distance in the Ar gas was longer (i.e. the creeping discharge could occur at a longer distance between the high-voltage electrode 712 and each of the members 716 and 721).

Given this result, the present inventor measured the SN ratio in each case where only one of the ground electrodes 713 and 714 above and below the high-voltage electrode 712 was made longer than the conventional ones. The result demonstrated that the SN ratio particularly improved when the downstream-side ground electrode 714 was made longer. A likely reason for this improvement is that, if the creeping discharge occurs in the downstream area of the flow of the plasma generation gas, i.e. in the area near the charge-collecting section, and causes the plasma generation area to expand into the downstream area, the collecting electrode provided for detecting the ion current in the charge-collecting section suffers from the mixing of electromagnetic noise due to the high voltage or an incidence of charged particles from the plasma.

Thus, a dielectric barrier discharge ionization detector according to one aspect of the present invention developed for solving the previously described problem is a dielectric barrier discharge ionization detector for ionizing and detecting a sample component in a sample gas by using plasma induced by an electric discharge within a gas passage through which a plasma generation gas containing argon is passed, the detector including:

a) a high-voltage electrode in which a surface facing the gas passage is covered with a dielectric body;

b) a ground electrode which is electrically connected to a ground and is arranged so as to face the gas passage, and in which a surface facing the gas passage is covered with a dielectric body at least over an upstream area in the flow direction of the plasma generation gas, where at least a portion of the surface covered with the dielectric body is located on the downstream side of the high-voltage electrode in the flow direction of the plasma generation gas;

c) an AC power source connected to the high-voltage electrode, for applying an AC voltage between the high-voltage electrode and the ground electrode so as to induce a dielectric barrier discharge within the gas passage and thereby generate plasma; and d) a charge-collecting section forming a section of the gas passage located downstream of a downstream end of the area of the ground electrode covered with the dielectric body, including a sample-gas introducer for introducing a sample gas into the downstream section and a collecting electrode for collecting ions generated from a sample component in the sample gas by light emitted from the plasma, where the length of the area of the ground electrode covered with the dielectric body on the downstream side of the high-voltage electrode is longer than the initiation distance for a creeping discharge between the high-voltage electrode and the charge-collecting section.

The phrase that "a surface facing the gas passage is covered with a dielectric body" in the present invention simply means that the surface concerned is separated from the gas passage by a dielectric body. The surface does not always need to be in contact with the dielectric body.

Figure 10:
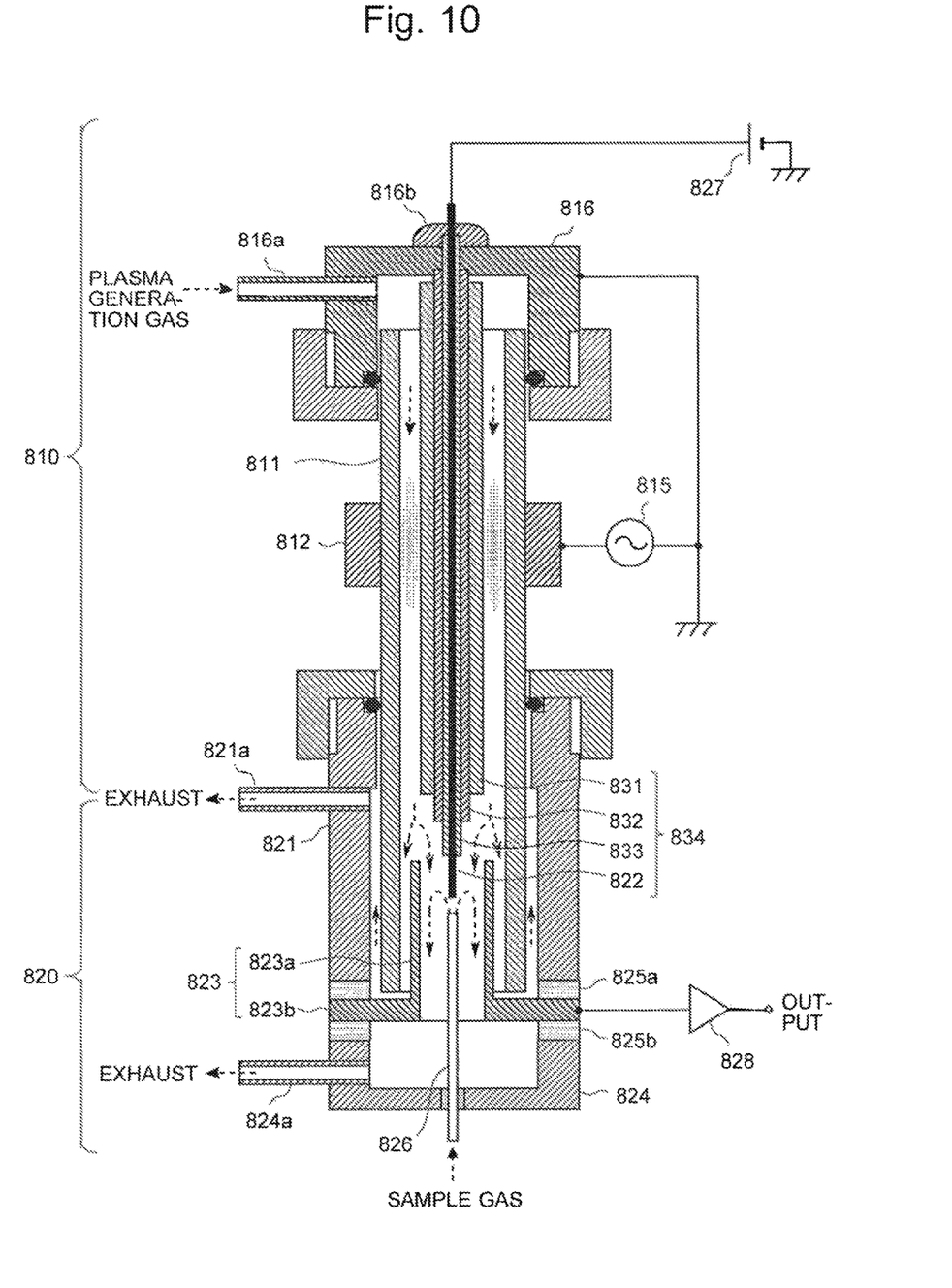
FIG. 10 is a schematic configuration diagram showing another configuration example of conventional BIDs.

The dielectric barrier discharge ionization detector according to the present invention is not limited to a configuration as shown in FIG. 8 in which a high-voltage electrode and two ground electrodes are circumferentially formed on the outer circumferential surface of a cylindrical dielectric tube; it can be applied in various structures of the dielectric barrier discharge ionization detectors. For example, the present invention can also be applied in a dielectric barrier discharge ionization detector disclosed in Patent Literature 3 (a schematic configuration of which is shown in FIG. 10), which includes a high-voltage electrode 812 circumferentially formed on the outer circumferential surface of an external dielectric tube 811 and an electrode structure 834 inserted into the external dielectric tube 811, the electrode structure 834 including an electrically grounded metallic tube 832 (which corresponds to the ground electrode in the present invention) covered with an internal dielectric tube 831 (this example will be detailed later).

When the present invention is applied in the dielectric barrier discharge ionization detector as shown in FIG. 8, the cylindrical dielectric tube 711 corresponds to both the dielectric body covering the high-voltage electrode and the dielectric body covering the ground electrode in the present invention. In other words, these dielectric bodies are formed as a single component. When the present invention is applied in the dielectric barrier discharge ionization detector as shown in FIG. 10, the external dielectric tube 811 corresponds to the dielectric body covering the high-voltage electrode in the present invention, while the internal dielectric tube 831 corresponds to the dielectric body covering the ground electrode in the present invention. In other words, these dielectric bodies are formed as separate components.

The "initiation distance for a creeping discharge between the high-voltage electrode and the charge-collecting section" in the present invention means the largest length of the ground electrode which allows the creeping discharge to occur between the high-voltage electrode and the charge-collecting section under the condition that the ground electrode covered with a dielectric body is located between the high-voltage electrode and the charge-collecting section. For example, in the Ar-BID having the discharging section 710 as shown in FIG. 8 in which the ground electrode 714 is arranged between the high-voltage electrode 712 and the charge-collecting section located downstream of the discharging section 710, if the length of the ground electrode 714 is gradually decreased while the high AC excitation voltage power source 715 is energized, a creeping discharge begins at a certain length, causing a sudden increase in the current value as measured between the high-voltage electrode 712 and the charge-collecting section (e.g. the connection member 721). The length of the ground electrode 714 at which such a sudden increase in the current value occurs is the initiation distance for the creeping discharge. The initiation distance for a creeping discharge depends on the frequency and amplitude of the low-frequency AC voltage, waveform of the power source, property of gas (gas purity), material of the dielectric body and other factors. Therefore, the "the length of the area, covered with the dielectric body of the ground electrode on the downstream side of the high-voltage electrode" in the present invention should be determined according to those parameters to be applied when the Ar-BID is in use.

Thus, in the dielectric barrier discharge ionization detector according to the present invention configured in the previously described manner, an occurrence of the creeping discharge between the high-voltage electrode and the charge-collecting section is prevented by separating the high-voltage electrode and the charge-collecting section from each other by the ground electrode which is covered with a dielectric body and which is longer than the initiation distance for the creeping discharge.

As noted earlier, in the dielectric barrier discharge ionization detector, as shown in the example of FIG. 8, the tube-line tip member 716 provided at the upper end of the discharging section 710 is also made of metal and electrically grounded. Therefore, the creeping discharge can develop into both upstream and downstream areas from the high-voltage electrode 712.

Thus, a dielectric barrier discharge ionization detector according to another aspect of the present invention is a dielectric barrier discharge ionization detector for ionizing and detecting a sample component in a sample gas by using plasma induced by an electric discharge within a gas passage through which a plasma generation gas containing argon is passed, the detector including:

a) a dielectric tube made of a dielectric material and containing an upstream section of the gas passage;

b) an electrically grounded tube-line tip member made of metal, for introducing the plasma generation gas into the dielectric tube;

c) a high-voltage electrode arranged on an outside of the dielectric tube;

d) an electrically grounded upstream-side ground electrode circumferentially arranged on the outside of the dielectric tube and located upstream of the high-voltage electrode as well as downstream of the tube-line tip member in the flow direction of the plasma generation gas;

e) an electrically grounded downstream-side ground electrode circumferentially arranged on the outside of the dielectric tube and located downstream of the high-voltage electrode in the flow direction of the plasma generation gas;

f) an AC power source connected to the high-voltage electrode, for applying an AC voltage between the high-voltage electrode and the upstream-side ground electrode as well as between, the high-voltage electrode and the downstream-side ground electrode so as to induce a dielectric barrier discharge within the gas passage and thereby generate plasma; and g) a charge-collecting section forming a downstream section of the gas passage and located downstream of the dielectric tube, including a sample-gas introducer for introducing a sample gas into the downstream section and a collecting electrode for collecting ions generated from a sample component in the sample gas by light emitted from the plasma, where one or both of the following conditions is satisfied; the length of the upstream-side ground electrode in the flow direction is longer than the initiation distance for a creeping discharge between the tube-line tip member and the high-voltage electrode; or the length of the area of the dielectric tube provided with the downstream-side ground electrode in the flow direction is longer than the initiation distance for a creeping discharge between the high-voltage electrode and the charge-collecting section.

In the previous description, that the high-voltage electrode, upstream-side ground electrode and downstream-side ground electrode are "arranged on an outside of the dielectric tube" means that those electrodes are provided at any place outside the dielectric tube where each electrode may be in contact with or separated from the outer wall surface of the dielectric tube. Furthermore, those electrodes do not always need to completely surround the dielectric tube along its circumference; they only need to be arranged so as to cover at least at a portion of the circumference of the dielectric tube.

For the purpose of improving the SN ratio, it is preferable make both of the upstream-side and downstream-side ground electrodes longer than the initiation distance for the creeping discharge on the upstream and downstream sides of the high-voltage electrode, respectively. However, it causes some problems, such as an increase in the entire length of the dielectric tube, as well, as the necessity to supply a considerably high voltage from the AC power source since a configuration for completely preventing the creeping discharge also impedes tire intended electric discharge between the high-voltage electrode and each of the upper and lower ground electrodes. Accordingly, the configuration in which only one of the ground electrodes is made longer also has practical merits.

Advantageous Effects of the Invention

As described to this point, the dielectric barrier discharge ionization detector (Ar-BID) according to the present invention configured in the previously described manner can suppress the creeping discharge and thereby prevent an expansion of the plasma generation area. As a result, the generation of the single-side barrier discharge mentioned earlier is prevented and the SN ratio is improved.

DESCRIPTION OF EMBODIMENTS

Modes for carrying out the present invention are hereinafter described using embodiments.

First Embodiment

Figure 1:
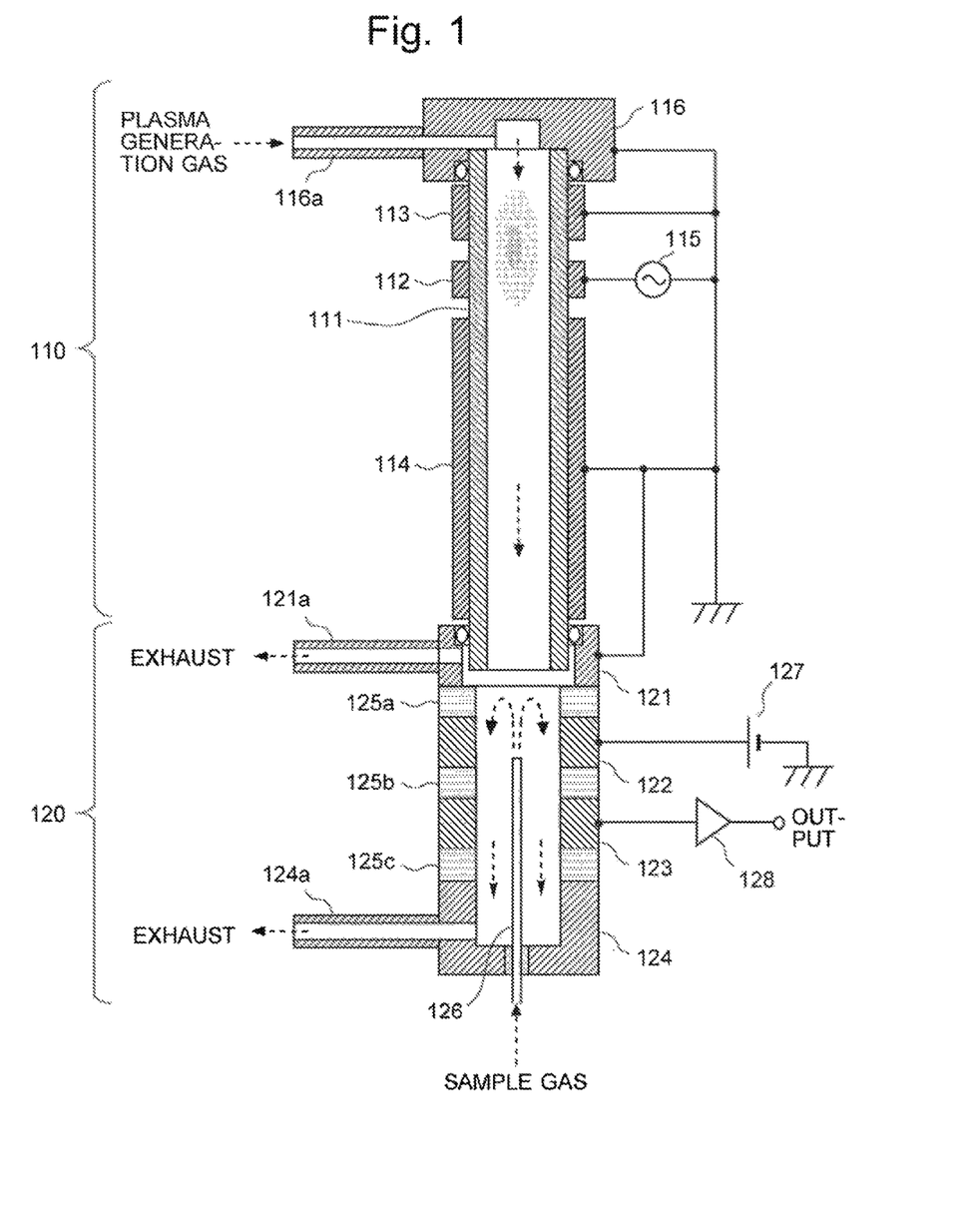
FIG. 1 is a schematic configuration diagram of an Ar-BID according to the first embodiment of the present invention.

FIG. 1 is a schematic configuration diagram of an Ar-BID according to one embodiment (first embodiment) of the present invention.

The Ar-BID of the present embodiment includes a cylindrical dielectric tube 111 through which a plasma generation gas is passed. In the following description, for convenience of explanation, the vertical direction is defined in such a manner that the upstream side in the flow direction of the gas (indicated by the downward arrows in FIG. 1) in the cylindrical dielectric tube 111 is called the "upper" side, and the downstream side is called the "lower" side. However, this definition does not limit the direction in which the Ar-BID should be used.

On the outer wall surface of the cylindrical dielectric tube 111, three ring-shaped electrodes made of an electric conductor (e.g. stainless steel or copper) are circumferentially formed at predetermined intervals of space along the flow direction of the gas.

Among the three electrodes, the central electrode 112 has a high AC excitation voltage power source 115 connected, while the two electrodes 113 and 114 located above and below the electrode 112 are both grounded. Hereinafter, the electrodes 112, 113 and 114 are called the "high-voltage electrode", "upstream-side ground electrode" and "downstream-side ground electrode", respectively, and these electrodes are collectively called the "plasma generation electrodes". The high AC excitation voltage power source 115 generates a high AC voltage at a frequency within a range of 1 kHz-100 kHz, more preferably, approximately 5 kHz-30 kHz (low frequency), with an amplitude of approximately 5 kV-10 kV. The AC voltage may have any waveform, such as a sinusoidal, rectangular, triangular or sawtooth wave.

In the Ar-BID of the present embodiment, the area above the lower end of the downstream-side ground electrode 114 in FIG. 1 is the discharging section 110, and the area below the lower end of the downstream-side ground electrode 114 is the charge-collecting section 120.

The cylindrical dielectric tube 111 has a tube-line tip member 116 at its upper end, to which a gas supply tube 116a is connected. Through this gas supply tube 116a, a plasma generation gas (Ar gas, or He gas with a trace amount of Ar gas added) doubling as a dilution gas is supplied into the cylindrical dielectric tube 111. Since the wall surface of the cylindrical dielectric tube 111 is present between the plasma generation gas and each of the plasma generation electrodes 112, 113 and 114, the wall surface itself functions as the dielectric coating layer which covers the surfaces of the plasma generation electrodes 112, 113 and 114, enabling dielectric barrier discharge to occur, as will be described later.

On the downstream side of the cylindrical dielectric tube 111, a connection member 121, bias electrode 122 and collecting electrode 123, all of which are cylindrical bodies having the same inner diameter, are arranged along the flow direction of the gas, with insulators 125a and 125b made of alumina, PTFE (polytetrafluoroethylene) resin or similar material inserted in between. On the downstream side of the collecting electrode 123, a tube-line end member 124 in the form of a cylindrical body with a closed bottom is attached via an insulator 125c. The inner space formed by the connection member 121, bias electrode 122, collecting electrode 123, tube-line end member 124 and insulators 125a, 125b and 125c communicates with the inner space of the cylindrical dielectric tube 111.

A bypass exhaust tube 121a for exhausting a portion of the plasma generation gas to the outside is connected to the circumferential surface of the connection member 121. A sample exhaust tube 124a is connected to the circumferential surface of the tube-line end member 124. A thin sample introduction tube 126 is inserted through the bottom of the tube-line end member 124. Through this sample introduction tube 126, a sample gas is supplied into the charge-collecting section 120. The charge-collecting section 120 is heated to a maximum temperature of approximately 450° C. by an external heater (not shown) in order to maintain the sample gas in the gasified state.

The connection member 121 is grounded and functions as a recoil electrode for preventing charged particles in the plasma carried by the gas stream from reaching the collecting electrode 123. The bias electrode 122 is connected to a bias DC power source 127. The collecting electrode 123 is connected to a current amplifier 128.

The operation for detecting a sample component contained in a sample gas in the present Ar-BID is hereinafter schematically described. As indicated by the rightward arrow in FIG. 1, a plasma generation gas doubling as a dilution gas is supplied through the gas supply tube 116a into the cylindrical dielectric tube 111. Since the BID according to the present embodiment is an Ar-BID, either an Ar gas or a He gas containing a trace amount of Ar gas is used as the plasma generation gas. The plasma generation gas flows downward through the cylindrical dielectric tube 111, a portion of which is exhausted through the bypass exhaust tube 121a to the outside, while the remaining portion serving as the dilution gas flows downward through the charge-collecting section 120, to be exhausted through the sample exhaust tube 124a to the outside. Meanwhile, the sample gas containing the sample component is supplied through the sample introduction tube 126 and ejected from the sample-gas ejection port at the end of the same tube into the charge-collecting section 120. Although the direction in which the sample gas is ejected from the sample-gas ejection port is opposite to the flow direction of the dilution gas, the sample gas is immediately pushed backward, being merged with the dilution gas and flowing downward, as indicated by the arrows in FIG. 1.

As noted earlier, while the plasma generation gas is flowing through the cylindrical dielectric tube 111, the high AC excitation voltage power source 115 applies a high AC voltage between the high-voltage electrode 112 and the upstream-side ground electrode 113 as well as between the high-voltage electrode 112 and the downstream-side ground electrode 114. As a result, a dielectric barrier discharge occurs within the cylindrical dielectric tube 111, whereby the plasma generation gas is ionized and a cloud of plasma (atmospheric-pressure non-equilibrium plasma) is generated. The excitation light emitted from the atmospheric-pressure non-equilibrium plasma travels through the discharging section 110 and the charge-collecting section 120 to the region where the sample gas is present, and ionizes the sample component in the sample gas. The thereby generated ions move toward the collecting electrode 123 due to the effect of the electric field created by the DC voltage applied to the bias electrode 122. Upon reaching the collecting electrode 123, the ions give electrons to or receive electrons from the same electrode. Consequently, an ion current corresponding to the amount of ions generated from the sample component by the action of the excitation light, i.e. an ion current corresponding to the amount of sample component, is fed to the current amplifier 128. The current amplifier 128 amplifies this current and produces a detection signal. In this manner, the Ar-BID according to the present embodiment produces a detection signal corresponding to the amount (concentration) of the sample component contained in the sample gas introduced through the sample introduction tube 126.

The basic components of the BID in the present embodiment are the same as those of commonly used BIDs. The previously described basic operation for detection is also similar to that of commonly used BIDs. The structural characteristic of the Ar-BID according to the present embodiment exists in that the length of the downstream-side ground electrode 114 is longer, for example, than that of the conventional Ar-BID shown in FIG. 8. The length of this ground electrode 114 is adjusted according to such parameters as the frequency and amplitude of the low-frequency AC voltage, waveform of the power source, property of gas and material of the dielectric body so that no creeping discharge will occur between the high-voltage electrode 112 and the charge-collecting section (e.g. connection member 121).

Figure 2:
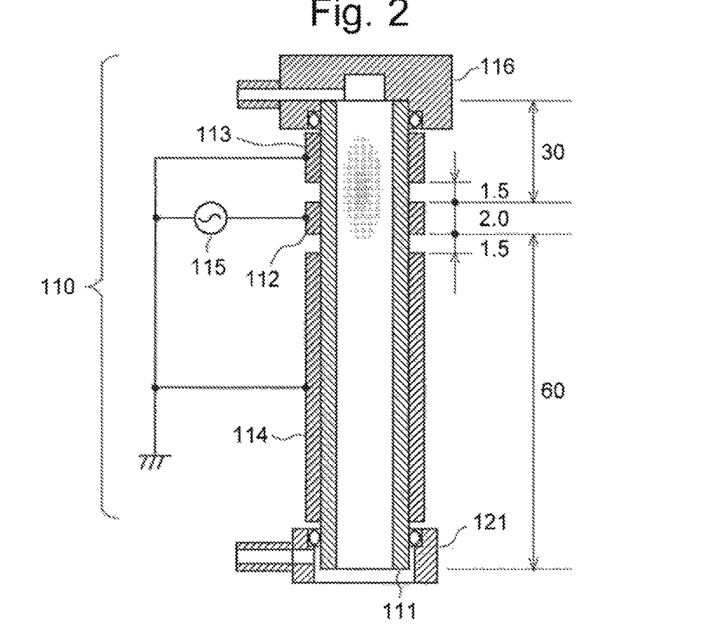
FIG. 2 shows one example of the electrode arrangement in the Ar-BID of the same embodiment.
Figure 3:
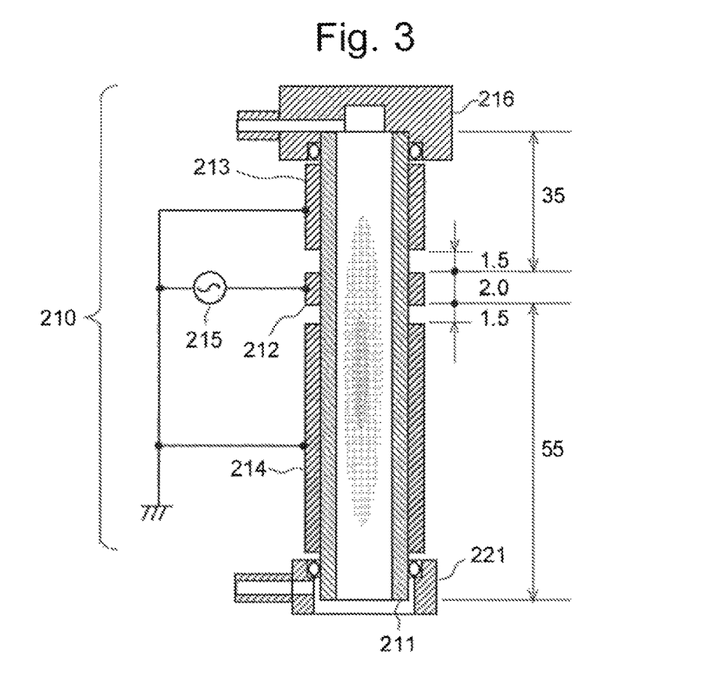
FIG. 3 shows the electrode arrangement in a comparative example.

FIG. 2 shows one specific example of the electrode arrangement in the discharging section 110 of the Ar-BID in the present embodiment. FIG. 3 shows the electrode arrangement of another discharging section 210 prepared for comparison. In FIG. 3, the components which have corresponding counterparts in FIG. 2 are denoted by numerals whose last two digits are the same as those of their respective counterparts. In each of those examples, the cylindrical dielectric tube 111 or 211 was made of a quartz tube measuring 4 mm in outer diameter, 2 mm in inner diameter and 92 mm in length. Strips of copper foil were wound on the outer circumferential surface of the quartz tube to form the high-voltage electrode 112 or 212, upstream-side ground electrode 113 or 213 and downstream-side ground electrode 114 or 214. Both of the high-voltage electrodes 112 and 212 had a length of 2 mm. The distance between the high-voltage electrode 112 or 212 and each ground electrode 113, 114, 213 or 214 was 1.5 mm. On the other hand, there is a difference between the configuration of FIG. 2 (which is hereinafter called the "present example") and that of FIG. 3 (which is hereinafter called the "comparative example") in terms of the distance between the end face on the upper side (gas introduction side) of the cylindrical dielectric tube 111 or 211 and the upper end of the high-voltage electrode 112 or 212; i.e., the distance was 30 mm in the present example and 35 mm in the comparative example. Consequently, the distance between the lower end of the high-voltage electrode 112 or 212 and the end face on the lower side (charge-collecting-section side) of the cylindrical dielectric tube 111 or 211 was 60 mm in the present example and 55 mm in the comparative example. In both configurations, the downstream-side ground electrode 114 or 214 extended to a position near the lower end of the cylindrical dielectric tube 111 or 211 (i.e. to a position immediately above the connection member 121 or 221). The length of the downstream-side ground electrode 114 or 214 was 45 mm in the present example and 40 mm in the comparative example.

In the Ar-BIDs having those discharging sections 110 and 210, while Ar gas (with a degree of purity of 99.9999% or higher) was continuously introduced into the cylindrical dielectric tube 111 or 211, the high AC excitation voltage power source 115 or 215 was energized to apply an AC high voltage having a sinusoidal current waveform at a frequency of approximately 40 kHz with a voltage amplitude of approximately 5 kVp-p. An observation of the two examples confirmed that the plasma in the present example was generated only on the upper side of the high-voltage electrode 112, whereas the plasma in the comparative example was spread over the entire length of the cylindrical dielectric tube 211.

Using each of the Ar-BIDs having those discharging sections 110 and 210 as the detector for GC, the sensitivity for a solution of a standard sample (dodecane) was measured. Additionally, the detection limit was calculated for each case from the measured noise value. Table 1 below shows the measured results and the calculated results based on the measured results.

TABLE 1

|  | Area of Plasma | Sensitivity (C/g) | Noise (fA) | Detection Limit (pg/sec) |
|---|---|---|---|---|
| Test Example | Upstream side only | 0.66 | 92 | 0.28 |
| Comparative Example | Entirety of discharge tube | 1.7 | 1060 | 1.25 |

According to Table 1, both the sensitivity and noise in the comparative example were higher than in the present example. A likely reason of this result is that the spreading of the plasma generation area into the vicinity of the charge-collecting section allowed a greater amount of excitation light from the plasma and charged particles in the plasma to enter the charge-collecting section and thereby increase the sensitivity, while the plasma which reached the connection member 221 caused the electric discharge to be a single-side barrier discharge, so that the plasma became more unstable and the amount of noise increased. By comparison, in the present example, although the sensitivity was lower than in the comparative example due to the small plasma generation area, the noise level was considerably lowered, and consequently, the detection limit was also better than the level recorded in the comparative example.

These results confirm that it is possible to prevent the expansion of the plasma generation area and thereby achieve a high level of SN ratio in an Ar-BID by sufficiently increasing the length of the ground electrode between the high-voltage electrode and the charge-collecting section.

The aforementioned effect is most likely due to the suppression of the creeping discharge between the high-voltage electrode and the charge-collecting section. As noted earlier, the initiation distance for the creeping discharge depends on such parameters as the frequency and amplitude of the low-frequency AC voltage, waveform of the power source, property of gas, and material of the dielectric body. Accordingly, the length of the ground electrode in the Ar-BID according to the present invention is not limited to the value in the previously described embodiment, but should be appropriately determined according to the configuration and use conditions of the Ar-BID. For example, under the condition that the various aforementioned parameters are fixed, the length of the downstream-side ground electrode may be variously changed to locate a point at which a sudden change occurs in a specific quantity, such as the size of the area where the plasma is generated (plasma generation area), amount of the current flowing between the high-voltage electrode 112 and the charge-collecting section (e.g. the connection member 121), or SN ratio during a sample measurement. The length of the ground electrode at the located point can be considered to correspond to the initiation distance for the creeping discharge. Therefore, by making the actual length of the downstream-side ground electrode larger than the length corresponding to the aforementioned point, the creeping discharge can be suppressed and a high SN ratio can be achieved. Furthermore, if the length of the ground electrode at which the creeping discharge ceases is previously investigated in the previously described manner with various values of the aforementioned parameters, it becomes possible to estimate the length of the ground electrode with which a high SN ratio can be achieved under a given condition.

Figure 4:
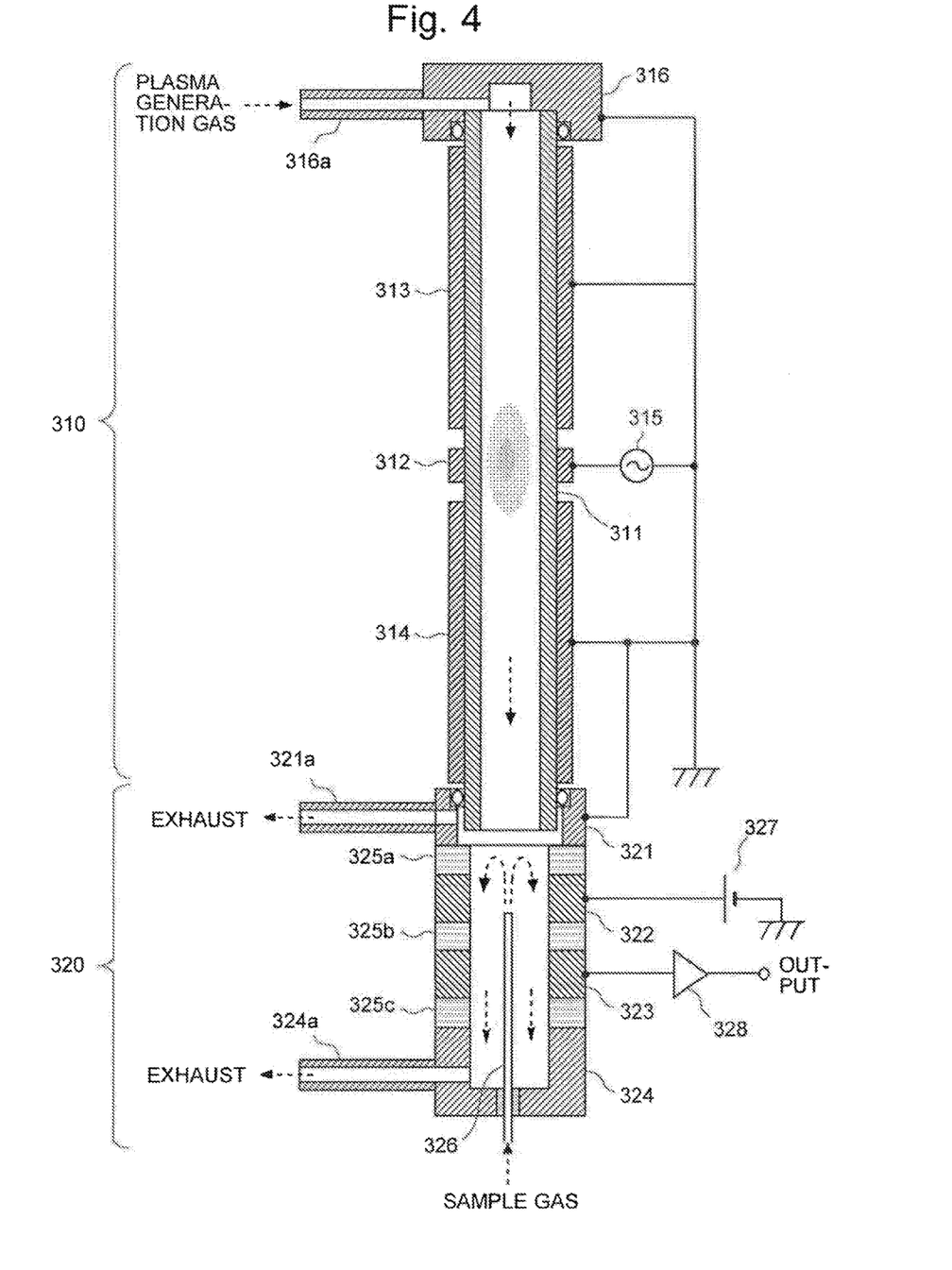
FIG. 4 is a schematic configuration diagram showing one example in which both of the two ground electrodes in the Ar-BID of the first embodiment are made longer than the creeping discharge initiation distance.

In the example of FIG. 1, only the downstream-side ground electrode is made longer than the initiation distance for the creeping discharge. It is also possible to make both of the upstream-side and downstream-side ground electrodes longer than the initiation distance for the creeping discharge. FIG. 4 shows a configuration example in such a case. The configuration example in FIG. 4 is identical to FIG. 1 except for the length of the upstream-side ground electrode 313. Accordingly, the corresponding components are denoted by numerals whose last two digits are common to both figures, and their descriptions will be appropriately omitted. In the example of FIG. 4, the downstream-side ground electrode 314 has a length that does not allow the creeping discharge to occur between the high-voltage electrode 312 and the charge-collecting section 320. The upstream-side ground electrode 313 also has a length that does not allow the creeping discharge to occur between the high-voltage electrode 312 and the tube-line tip member 316. Although the entire length of the discharging section 310 increases, such a configuration, advantageously suppresses both creeping discharges which develop from the high-voltage electrode 312 into the upstream and downstream directions, so that an even higher level of SN ratio can be achieved.

Figure 5:
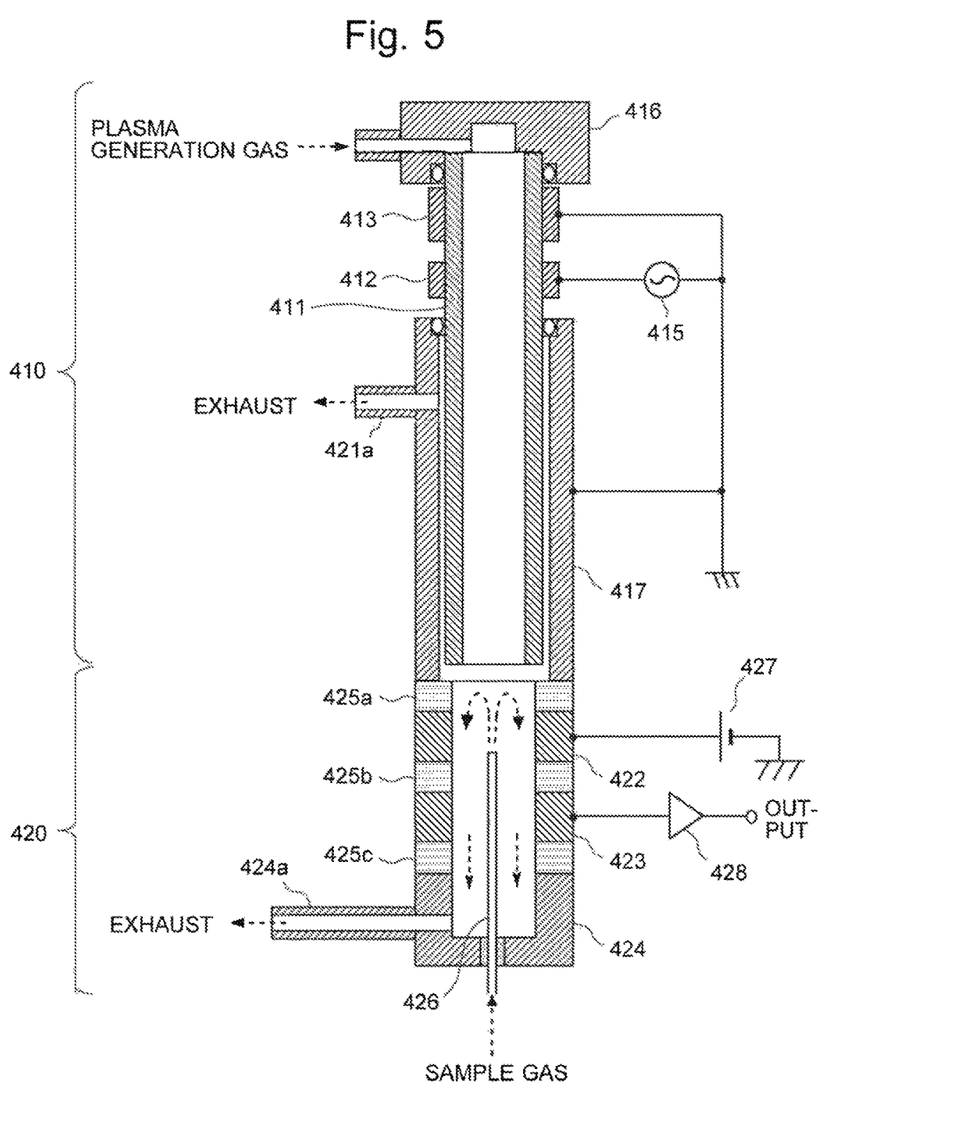
FIG. 5 shows another configuration example of the Ar-BID according to the first embodiment.

In the Ar-BID according to the present invention, the connection member which connects the cylindrical dielectric tube to the charge-collecting section may be combined with the downstream-side ground electrode into a single component. FIG. 5 shows one example of the Ar-BID having such a configuration (in FIG. 5, the components which have identical or corresponding counterparts in FIG. 1 are denoted by numerals whose last two digits are the same as those of their respective counterparts, and their descriptions will be appropriately omitted). The Ar-BID in FIG. 5 corresponds to the configuration obtained by removing the downstream-side ground electrode 114 from FIG. 1 and extending the connection member 121 over the area where the downstream-side ground electrode 114 was previously provided. This member in FIG. 5 which corresponds to the extended connection member 121 is hereinafter called the "tubular member" 417. The tubular member 417 is electrically grounded, has a bypass exhaust tube 421a connected to its circumferential surface, and surrounds the outer circumferential surface of the cylindrical dielectric tube 411, leaving a narrow gap in between for allowing a passage of gas. With such a configuration, the tubular member 417 can fulfill the functions of both the connection member 121 in FIG. 1 and the downstream-side ground electrode 114 in the same figure.

In this example, the area on the upstream side of the lower end of the dielectric tube 411 in FIG. 5 is the discharging section 410, while the area on the downstream side of the lower end of the dielectric tube 411 is the charge-collecting section 420. In the example of FIG. 5, the length of the area of the dielectric tube 411 surrounded by the tubular member 417 (which corresponds to the downstream-side ground electrode) on the downstream side of the high-voltage electrode 412 is made longer than the initiation distance for the creeping discharge between the high-voltage electrode 412 and the charge-collecting section 420. Additionally, the upstream-side ground electrode 413 may also be made longer than the initiation distance for the creeping discharge, as shown in FIG. 4. It is also possible to make only the upstream-side ground electrode 413 longer than the initiation distance for the creeping discharge.

Second Embodiment

Figure 6:
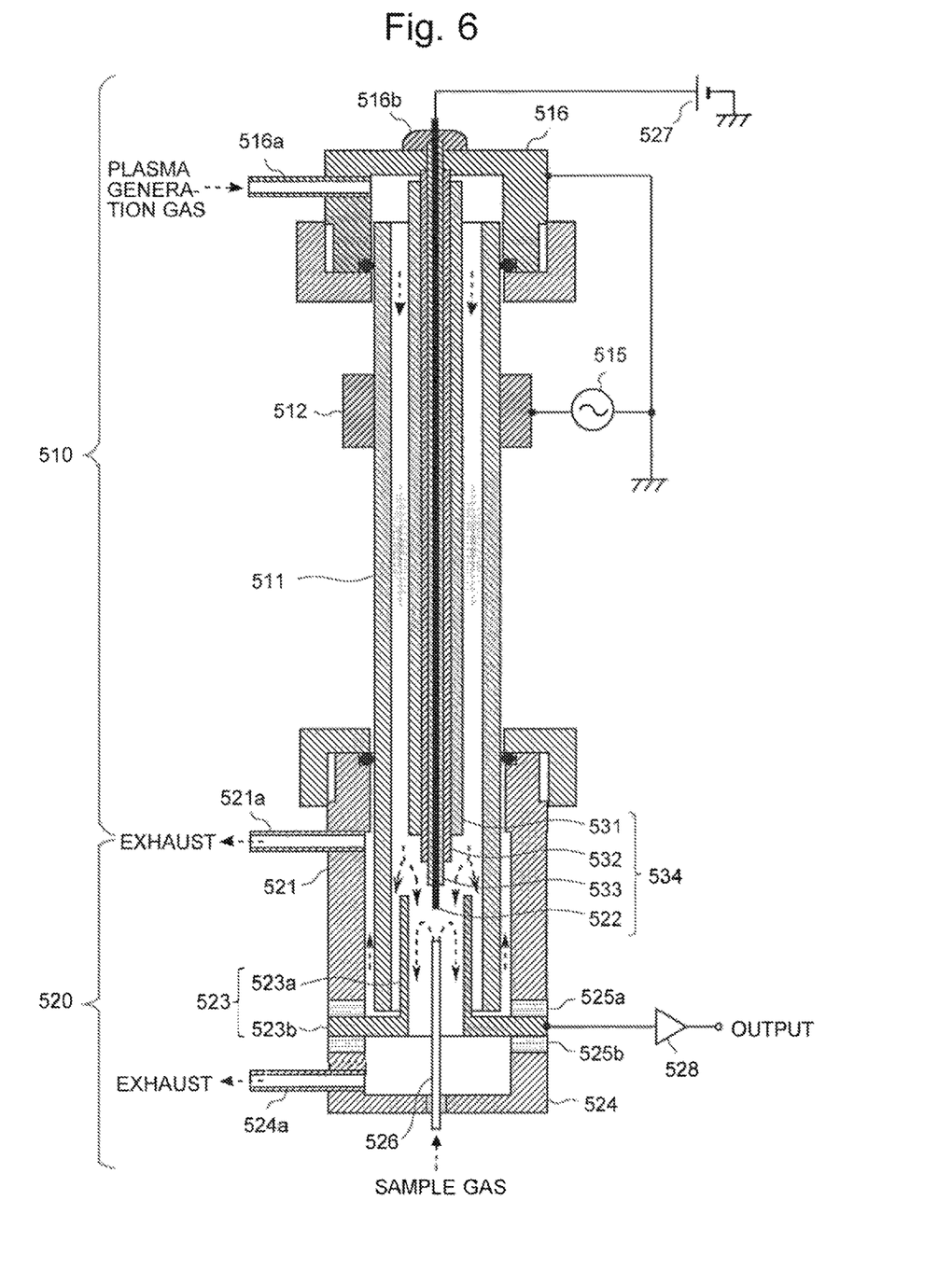
FIG. 6 is a schematic configuration diagram of an Ar-BID according to the second embodiment of the present invention.

Another embodiment (second embodiment) of the Ar-BID according to the present invention is hereinafter described with reference to FIG. 6. FIG. 6 is a schematic configuration diagram of the Ar-BID according to the present embodiment.

The Ar-BID of the present embodiment includes an external dielectric tube 511 made of a dielectric material, such as quartz. For example, a quartz tube measuring 7 mm in outer diameter and 5 mm in inner diameter can be used as the external dielectric tube 511. A ring-shaped electrode 512 made of metal (e.g. stainless steel or copper) is circumferentially formed on the outer circumferential surface of the external dielectric tube 511.

At the upper end of the external dielectric tube 511, a tube-line tip member 516 having a cylindrical shape with a closed top and an open bottom is attached. A gas supply tube 516a is connected to the circumferential surface of the tube-line tip member 516. The tube-line tip member 516 and the supply tube 516a are made of metal, such as stainless steel.

Inside the external dielectric tube 511, an internal dielectric tube 531 made of a dielectric material (e.g. quartz) is arranged, and a metallic tube 532 made of metal (e.g. stainless steel) is inserted into this internal dielectric tube 531. Furthermore, an insulating tube 533 made of alumina or the like is inserted into the metallic tube 532, and a metallic wire 522 made of metal (e.g. stainless steel) is inserted into the insulating tube 533. The internal dielectric tube 531, metallic tube 532, insulating tube 533 and metallic wire 522 have their respective lengths sequentially increased in the mentioned order, with the upper and lower ends of the metallic tube 532 protruding from the upper and lower ends of the internal dielectric tube 531, and the upper and lower ends of the insulating tube 533 protruding from the upper and lower ends of the metallic tube 532. The upper and tower ends of the metallic wire 522 also protrude from the upper and lower ends of the insulating tube 533. The structure composed of the internal dielectric tube 531, metallic tube 532, insulating tube 533 and metallic wire 522 is hereinafter called the "electrode structure" 534.

The tube-line tip member 516 has a through hole formed in its upper portion. The upper end of the metallic tube 532 is fixed in this through hole by welding or soldering. The insulating tube 533 and the metallic wire 522 are extracted to the outside from the through hole in the upper portion of the tube-line tip member 516, and sealed and fixed on the upper surface of the tube-line tip member 516 with a gas-tight adhesive 516b.

The tube-line tip member 516 is electrically grounded through an electric line (or gas supply tube 516a), whereby the metallic tube 532 is also electrically grounded via the tube-line tip member 516. On the other hand, the ring-shaped electrode 512 has a high AC excitation voltage power source 515 connected to it. That is to say, in the Ar-BID of the present embodiment, the ring-shaped electrode 512 corresponds to the high-voltage electrode in the present invention, the area of the metallic tube 532 covered with the internal dielectric tube 531 (this area is hereinafter called the "dielectric coverage area") corresponds to the ground electrode in the present invention, and the ring-shaped electrode (high-voltage electrode) 512 and the dielectric coverage area of the metallic tube 532 (ground electrode) function as the plasma generation electrodes. The inner circumferential surface of the ring-shaped electrode 512 faces a portion of the outer circumferential surface of the metallic tube 532 across the wall surfaces of the external dielectric tube 511 and the internal dielectric tube 531. Accordingly, those dielectric wail surfaces themselves function as dielectric coating layers which cover the surfaces of the plasma generation electrodes (i.e. ring-shaped electrode 512 and metallic tube 532), enabling a dielectric barrier discharge to occur.

In the present embodiment, the area above the lower end of the internal dielectric tube 531 in FIG. 6 corresponds to the discharging section 510, and the area below the lower end of the internal dielectric tube 531 corresponds to the charge-collecting section 520.

The lower end of the external dielectric tube 511 is inserted into the cylindrical connection member 521. A bypass exhaust tube 521a made of metal (e.g. stainless steel) is provided on the circumferential surface of the connection member 521.

Below the connection member 521, there are a cylindrical insulating member 525a, flanged metallic tube 523, cylindrical insulating member 525b, and tube-line end member 524 arranged in the mentioned order. The flanged metallic tube 523 has a cylindrical portion 523a and a flange portion 523b which is formed at the lower end of the cylindrical portion 523a and extends outward in the radial direction of the cylindrical portion 523a. The cylindrical portion 523a has an outer diameter smaller than the inner diameter of the external dielectric tube 511 and is inserted in the external dielectric tube 511 from below. The flange portion 523b, which has approximately the same outer diameter as those of the connection member 521, insulating members 525a, 525b and tube-line end member 524, is held between the lower end of the connection member 521 and the upper end of the tube-line end member 524 via the insulating members 525*a* and 525*b*. The connection member 521, tube-line end member 524 and flanged metallic tube 523 are all made of metal (e.g. stainless steel). The connection member 521, insulating member 525*a*, flanged metallic tube 523, insulating member 525*b*, and tube-line end member 524 are each adhered to the neighboring members with a heat-resistant ceramic adhesive.

The tube-line end member 524 is a cylindrical member having an open top and a closed bottom, with a sample exhaust tube 524*a* made of metal (e.g. stainless steel) connected to its circumferential surface. A through hole is formed in the bottom surface of the tube-line end member 524, and a sample introduction tube 526 connected to the exit end of a GC column (or similar element) is inserted into the through hole. The sample introduction tube 526 is pulled into the cylindrical portion 523*a* of the flanged metallic tube 523. The upper end (i.e. sample-gas exit port) of the sample introduction tube 526 is located at a vertical position between the upper and lower ends of the cylindrical portion 523*a*.

As described earlier, a portion which is not covered with the insulating tube 533 ("exposed portion") is provided at the lower end of the metallic wire 522 in the electrode structure 534. The exposed portion is inserted into the cylindrical portion 523*a* of the flanged metallic tube 523 from above and is located near the upper end of the cylindrical portion 523*a*. As a result, the exposed portion of the metallic wire 522 is located directly above the sample-gas exit port. Furthermore, the metallic wire 522 is extracted, from the tube-line tip member 516 to the outside and connected to a bias DC power source 527. The flanged metallic tube 523 is connected to a current amplifier 528. That is to say, in the Ar-BID of the present embodiment) the exposed portion at the lower end of the metallic wire 522 functions as the bias electrode, while the cylindrical portion 523*a* of the flanged metallic tube 523 functions as the ion-collecting electrode. Accordingly, the space between the inner wall of the cylindrical portion 523*a* and the exposed portion of the metallic wire 522 is the effective ion-collecting area.

As noted earlier, the metallic tube 532 included in the electrode structure 534 is grounded via the tube-line tip member 516, and a portion which is not covered with the internal dielectric tube 531 ("exposed portion") is provided at the lower end of the metallic tube 532. This exposed portion is located directly above the flanged metallic tube 523 and functions as a recoil electrode for preventing charged particles in the plasma from reaching the ion-collecting electrode (i.e. the cylindrical portion 523*a*).

A detecting operation by the present Ar-BID is hereinafter described. As indicated by the rightward arrow in FIG. 6, a plasma generation gas (Ar gas, or He gas containing a trace amount of Ar gas) doubling as a dilution gas is supplied through the gas supply tube 516*a* into the tube-line tip member 516.

The plasma generation gas doubling as the dilution gas flows downward through the space between the inner wall of the external dielectric tube 511 and the outer wall of the internal dielectric tube 531. At the upper end of the cylindrical portion 523*a* of the flanged metallic tube 523, a portion of the gas is made to branch off. The branch portion of the plasma generation gas flows downward through the space between the inner wall of the external dielectric tube 511 and the outer wall of the cylindrical portion 523*a*. At the lower end of the external dielectric tube 511, the flow turns outward, and then upward. After flowing upward through the space between the outer wall of the external, dielectric tube 511 and the inner wall of the connection member 521, the gas is exhausted through the bypass exhaust tube 521*a* to the outside. Meanwhile, the remaining portion of the plasma generation gas flows into the space surrounded by the inner wall of the cylindrical portion 523*a*, as the dilution gas to be mixed with the sample gas.

While the plasma generation gas is flowing through the space between the inner wall of the external dielectric tube 511 and the outer wall of the internal dielectric tube 531 in the previously described manner, the high AC excitation voltage power source 515 is energized. The high AC excitation voltage power source 515 applies a low-frequency high AC voltage between the plasma generation electrodes, i.e. the ring-shaped electrode (high-voltage electrode) 512 and the dielectric coverage area (ground electrode) of the metallic tube 532. Consequently, an electric discharge occurs within the area sandwiched between the ring-shaped electrode 512 and the dielectric coverage area of the metallic tube 532. This electric discharge is induced through the dielectric coating layers (external dielectric tube 511 and internal dielectric tube 531), and therefore, is a dielectric barrier discharge. By this dielectric barrier discharge, the plasma generation gas flowing through the space between the inner wall of the external dielectric tube 511 and the outer wall of the internal dielectric tube 531 is ionized, forming a cloud of plasma (atmospheric-pressure non-equilibrium plasma).

The excitation light emitted from the atmospheric-pressure non-equilibrium plasma travels through the space between the inner wall of the external dielectric tube 511 and the outer wall of the internal dielectric tube 531 to the region where the sample gas is present, and ionizes the molecules (or atoms) of the sample component in the sample gas. The thereby generated sample ions are gathered to the ion-collecting electrode (i.e. the cylindrical portion 523*a* of the flanged metallic tube 523) due to the electric field created by the bias electrode (i.e. the exposed portion of the metallic wire 522) located directly above the sample-gas exit port, to be eventually detected as a current output. Consequently, an ion current corresponding to the amount of generated sample ions, i.e. an ion current corresponding to the amount of sample component is fed to the current amplifier 528. The current amplifier 528 amplifies this current and provides it a detection signal. In this manner, the present Ar-BID produces a detection signal corresponding to the amount (concentration) of the sample component contained in the introduced sample gas.

In FIG. 6, the metallic wire 522 is made to function as the bias electrode, and the flanged metallic tube 523 is made to function as the ion-collecting electrode. Their functions may be transposed. That is to say, the metallic wire 522 may be connected to the current amplifier 528, and the flanged metallic tube 523 may be connected to the bias DC power source 527. It is also possible to replace the flanged metallic tube 523 with an element similar to the cylindrical metallic electrode 122 or 123 provided in the charge-collecting section in FIG. 1, and make this element function as the ion-collecting electrode or bias electrode.

The basic components and detecting operation of the Ar-BID in the present embodiment are the same as those of the BID described in Patent Literature 3. FIG. 10 shows the configuration of the BID described in Patent Literature 3. In FIG. 10, the components which are common to FIGS. 6 and 10 are denoted by numerals whose last two digits are common to both figures.

The structural characteristic of the Ar-BID of the present embodiment exists in that the distance from the lower-end of position of the high-voltage electrode (i.e. ring-shaped electrode 512) to the lower-end position of the internal dielectric tube 531 in the flow direction of the gas is larger than that of the conventional Ar-BID as shown in FIG. 10. The external dielectric tube 511 and the electrode structure 534 are also made to be correspondingly longer. As noted earlier, the dielectric coverage area of the metallic tube 532 corresponds to the "ground electrode" in the present invention. Therefore, by making the electrode structure 534 sufficiently long, the length of the ground electrode on the downstream side of the lower end of the high-voltage electrode (ring-shaped electrode 512) can be long enough to prevent an occurrence of the creeping discharge between the high-voltage electrode 512 and the charge-collecting section 520 (specifically, for example, the lower-end area of the metallic tube 532 which is not covered with the inner dielectric tube 531, or the upper-end portion of the flanged metallic tube 523). The length of the ground electrode, i.e. the length of the metallic tube 532 and that of the internal dielectric tube 531, should be adjusted to be longer than the initiation distance for the creeping discharge determined by such parameters as the frequency and amplitude of the low-frequency AC voltage, waveform of the power source, property of gas and material of the dielectric body.

Figure 7:
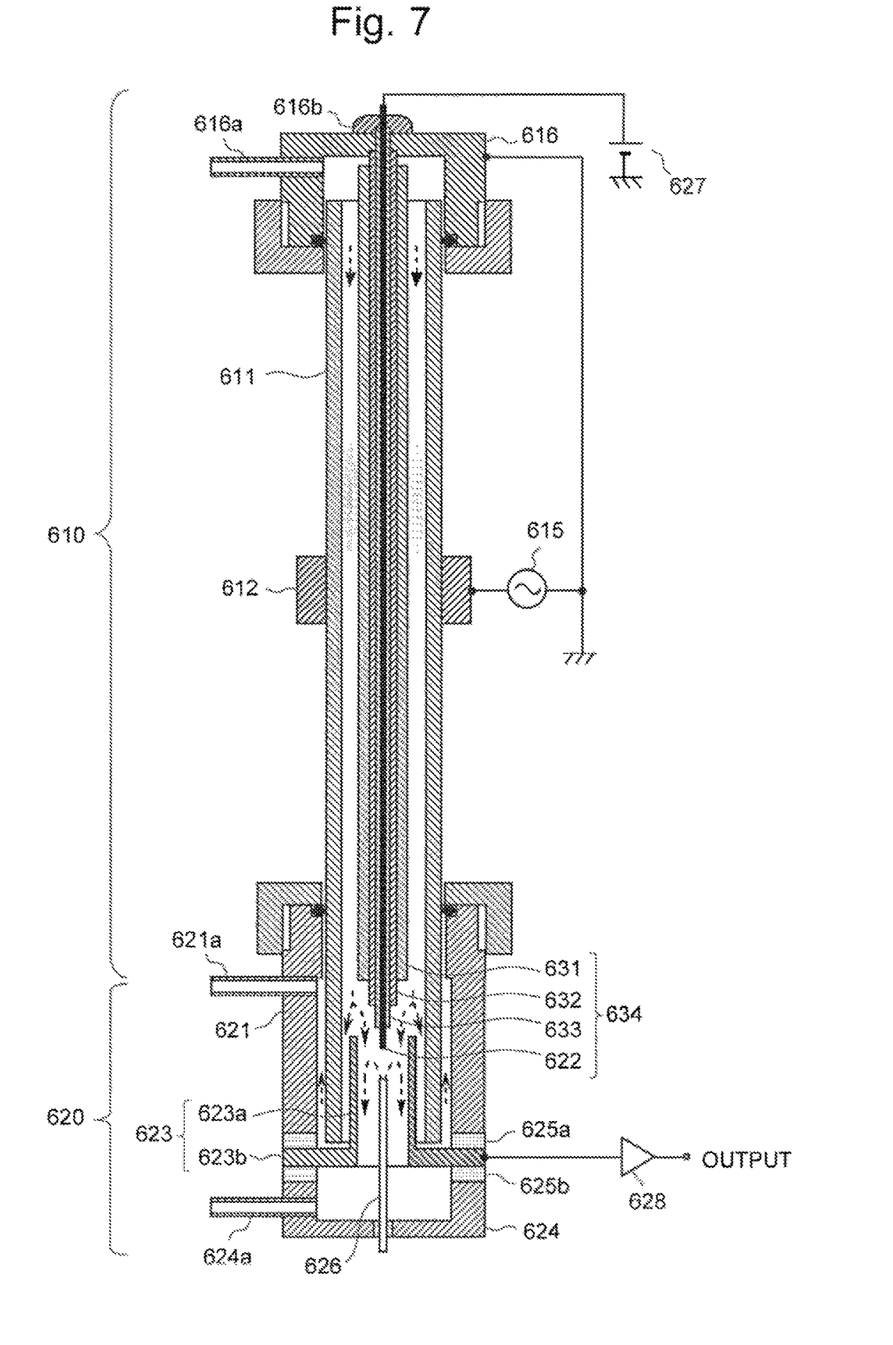
FIG. 7 is a schematic configuration diagram showing another configuration example of the Ar-BID according to the second embodiment of the present invention.

In the example of FIG. 6, only the distance from the lower end of the high-voltage electrode (ring-shaped electrode 512) to the lower end of the dielectric coverage area of the metallic tube 532 is made longer than the initiation distance for the creeping discharge. It is also possible to additionally make the distance from the upper end of the high-voltage electrode (ring-shaped electrode 512) to the lower end of the tube-line tip member 516 longer than the initiation distance for the creeping discharge. FIG. 7 shows a configuration example in such a case. In FIG. 7, the components which have corresponding counterparts in the configuration shown in FIG. 6 are denoted by numerals whose last two digits are the same as those of their respective counterparts. The configuration example in FIG. 7 is identical to FIG. 6 except for the length of the external dielectric tube 611 as well as the distance from the upper end of the ring-shaped electrode 612 to the lower end of the tube-line tip member 616. Although the entire length of the discharging section 610 increases, such a configuration advantageously suppresses both creeping discharges which develop from the high-voltage electrode 612 into the upstream and downstream directions, so that an even higher level of SN ratio can be achieved.

REFERENCE SIGNS LIST 110, 510 . . . Discharging Section
111 . . . Cylindrical Dielectric Tube
112 . . . High-Voltage Electrode
113 . . . Upstream-Side Ground Electrode
114 . . . Downstream-Side Ground Electrode
115, 515 . . . High AC Excitation Voltage Power Source
116, 516 . . . Tube-Line Tip Member
120, 520 . . . Charge-Collecting Section
121, 521 . . . Connection Member
122 . . . Bias Electrode
123 . . . Collecting Electrode
124, 524 . . . Tube-Line End Member
126, 526 . . . Sample Introduction Tube
127, 527 . . . Bias DC Power Source
128, 528 . . . Current Amplifier
511 . . . External Dielectric Tube
512 . . . Ring-Shaped Electrode
522 . . . Metallic Wire
523 . . . Flanged Metallic Tube
523a . . . Cylindrical Portion
523b . . . Flange Portion
531 . . . Internal Dielectric Tube
532 . . . Metallic Tube
533 . . . Insulating Tube
534 . . . Electrode Structure

The invention claimed is:

1. A dielectric barrier discharge ionization detector for ionizing and detecting a sample component in a sample gas by using plasma induced by an electric discharge within a gas passage through which a plasma generation gas containing argon is passed, the detector comprising:
   a) a high-voltage electrode in which a surface facing the gas passage is covered with a dielectric body;
   b) a ground electrode which is electrically connected to a ground and is arranged so as to face the gas passage, and in which a surface facing the gas passage is covered with a dielectric body at least over an upstream area in a flow direction of the plasma generation gas, where at least a portion of the surface covered with the dielectric body is located on a downstream side of the high-voltage electrode in the flow direction of the plasma generation gas;
   c) an AC power source connected to the high-voltage electrode, for applying an AC voltage between the high-voltage electrode and the ground electrode so as to induce a dielectric barrier discharge within the gas passage and thereby generate plasma; and
   d) a charge-collecting section forming a section of the gas passage located downstream of a downstream end of the area of the ground electrode covered with the dielectric body, including a sample-gas introducer for introducing a sample gas into the downstream section and a collecting electrode for collecting ions generated from a sample component in the sample gas by light emitted from the plasma,
   where a length of the area of the ground electrode covered with the dielectric body on the downstream side of the high-voltage electrode is longer than a predetermined initiation distance for a creeping discharge between the high-voltage electrode and the charge-collecting section, and
   wherein the predetermined initiation distance is determined based on at least one parameter of a frequency of the AC voltage and an amplitude of the AC voltage, a waveform of the AC voltage, a property of the plasma generation gas and a material of the dielectric body.

2. A dielectric barrier discharge ionization detector for ionizing and detecting a sample component in a sample gas by using plasma induced by an electric discharge within a gas passage through which a plasma generation gas containing argon is passed, the detector comprising:
   a) a dielectric tube made of a dielectric material and containing an upstream section of the gas passage;
   b) an electrically grounded tube-line tip member made of metal, for introducing the plasma generation gas into the dielectric tube;
   c) a high-voltage electrode circumferentially arranged on an outside of the dielectric tube;

d) an electrically grounded upstream-side ground electrode circumferentially arranged on the outside of the dielectric tube and located upstream of the high-voltage electrode as well as downstream of the tube-line tip member in a flow direction of the plasma generation gas;

e) an electrically grounded downstream-side ground electrode circumferentially arranged on the outside of the dielectric tube and located downstream of the high-voltage electrode in the flow direction of the plasma generation gas;

f) an AC power source connected to the high-voltage electrode, for applying an AC voltage between the high-voltage electrode and the upstream-side ground electrode as well as between the high-voltage electrode and the downstream-side ground electrode so as to induce a dielectric barrier discharge within the gas passage and thereby generate plasma; and g) a charge-collecting section forming a downstream section of the gas passage and located downstream of the dielectric tube, including a sample-gas introducer for introducing a sample gas into the downstream section and a collecting electrode for collecting ions generated from a sample component in the sample gas by light emitted from the plasma, where one or both of following conditions is satisfied: a length of the upstream-side ground electrode in the flow direction is longer than a first predetermined initiation distance for a creeping discharge between the tube-line tip member and the high-voltage electrode; or a length of the area of the dielectric tube provided with the downstream-side ground electrode in the flow direction is longer than a second predetermined initiation distance for a creeping discharge between the high-voltage electrode and the charge-collecting section, and wherein the first and second predetermined initiation distances are determined based on at least one parameter of a frequency of the AC voltage and an amplitude of the AC voltage, a waveform of the AC voltage, a property of the plasma generation gas and a material of the dielectric body.

* * * * *